United States Patent [19]
Bigelis et al.

[11] Patent Number: 4,877,728
[45] Date of Patent: Oct. 31, 1989

[54] BIOTRANSFORMATION OF L-TYROSINE AND L-PHENYLALANINE TO 2,5-DIHYDROXYPHENYLACETIC ACID FOLLOWED BY POLYMERIZATION TO MELANIN PIGMENTS

[75] Inventors: Ramunas Bigelis, Elkhart; Kathleen A. Black, Bristol, both of Ind.

[73] Assignee: Miles Inc., Elkhart, Ind.

[21] Appl. No.: 172,770

[22] Filed: Mar. 28, 1988

[51] Int. Cl.[4] .................... C12P 21/00; C12P 21/06; C12P 7/42
[52] U.S. Cl. .................................. 435/68; 435/42; 435/69; 435/108; 435/146; 435/171; 435/911
[58] Field of Search ............... 435/42, 146, 171, 68, 435/69, 108, 911

[56] References Cited

U.S. PATENT DOCUMENTS 3,551,438 12/1970 Oediger et al. ............... 260/297
4,182,720  1/1980 Renfrew et al. ............... 260/343.3
4,479,803 10/1984 Bachmann et al. ............ 8/406

OTHER PUBLICATIONS

Derwent Abs. 87-129791/19 DD-242055, 1-87.
CA 88(19) 133020v Yuasa et al., 1978.
CA 107(17) 152919x Schellenberger et al., DD-242055.
CA 99(1) (4028) Iske et al., Acta Biotech 3(2) 14353 (1983).
Japio Derwent Abs. 80-023976 J55023976, Abe et al., 2-1980.
Derwent Abs. 66-26907f/00 J69006633, Taked Chem, 1968.
Derwent Abs. 80-24274c/14, BioRes J55023976, 2-1980.
Derwent Abs. 78-535676a/30 DD-130046, 3-1976.
Bassel et al., *J. Bacteriol.*, 123 (1), 1975, pp. 118-122 "Mutant of the Yeast Saccharomycopsis Lipolytica that Accumulates and Excretes Protoporphyrin IX".
Yoshizaki et al., *Agric. Biol. Chem.*, 49 (3), 1985, pp. 877-879, "The Formation of 2,6-Dihydroxyphenylacetic Acid from Phenylacetic Acid by Various Fungi".
Neuberger et al., *Biochem. J.*, 41, 1947, pp. 438-449, "Studies on Alcaptonuria-2, Investigations on a Case of Human Alcaptonuria."
Neuberger and Webster, *Biochem. J.*, 41, 1947, pp. 449-457, "Studies on Alcaptonuria-3., Experimental Alcaptonuria in Rats."
Morrissey, J. H., *J. Gen. Microbiol.*, 129, pp. 1127-1132—"Deficiency in Homogentisic Acid Oxidase Activity Associated with the Brown Phenotype of *Dictyostelium Discoideum*".
Katz & Sussman, *Proc. Nat. Acad. Sci.* U.S.A., 69, pp. 495-498, 1972, "Parasexual Recombination in *Dictyostelium Discoideum*: Selection of Stable Diploid Heterozygotes and Stable Haploid Segregants".
Sussman & Sussman, *J. Gen. Microbiol.*, 30, pp. 349-355, 1963, "Ploidal Inheritance in the Slime Mould *Dictyostelium Discoideum*: Haploidization and Genetic Segragation of Diploid Strains".

*Primary Examiner*—Herbert J. Lilling
*Attorney, Agent, or Firm*—Jerome L. Jeffers

[57] ABSTRACT

Disclosed is a method for the production of homogentisic acid which involves growing a fungus (typically a yeast of the species *Yarrowia lipolytica*) which has been mutated to provide a strain which is unable to grow on L-tyrosine and/or L-phenylalanine as the sole carbon source in a suitable growth medium containing L-tyrosine and/or L-phenylalanine together with a sub-optimal concentration of carbohydrate assimilable by the yeast. The yeast secretes recoverable quantities of homogentisic acid which can be rapidly and completely polymerized by raising the pH of the medium to above 10 thereby forming a melanin pigment.

3 Claims, No Drawings

BIOTRANSFORMATION OF L-TYROSINE AND L-PHENYLALANINE TO 2,5-DIHYDROXYPHENYLACETIC ACID FOLLOWED BY POLYMERIZATION TO MELANIN PIGMENTS

BACKGROUND OF THE INVENTION

It is reported by Bassel et al. *J. Bacteriol.*, 123(1), 1975, Pp. 118;14 122 that the accumulation of porphyrins has been observed in many microbial species including both photosynthetic and heterotrophic bacteria, yeast and protozoa. In particular, they report a mutant of the yeast *Saccharomycopsis lipolytica* a sexual form of *Candida lipolytica* (now termed *Yarrowia lipolytica*) that accumulates andsecretes protoporphyrin IX.

Yashizako et al. report in *Agric. Biol. Chem.*, 49(3), 1985, Pp. 877–879 that the ability to convert phenylacetic acid to 2,5-dihydroxyphenylacetic acid (homogentisic acid-HA) is widely present in fungi. They report experimentation with fungi of the genera Aspergillus Penicillium, Gibberella, Fusarium, Miucor, Rhizopus, Helminthosporium, Cylindrocarpon, Neurospora, Cephalosporium, Chaetomidium, Mortierella, Phellinus, Pellicularia, and Byssochlamys.

Amides and esters of homogentisic acid are described as being useful in the oxidative dyeing of hair in U.S. Pat. No. 4,479,803.

In U.S. Pat. No. 4,182,720 there is disclosed a chemical process for preparing homogentisic lactone, a precursor of homogentisic acid which the patentees characterize as being of value as a photographic dye developer and as an intermediate in the manufacture of dyestuffs and pharmaceuticals.

Oediger et al. disclose in U.S. Pat. No. 3,551,438 the reaction of homogentisic acid lactone with certain amines to produce homogentisic acid or amine derivatives thereof which exhibit strong and long lasting choleretic activity with low toxicity.

DESCRIPTION OF THE INVENTION

Biochemical blocks caused by genetic mutations are known to cause accumulation of metabolic intermediates. Alcaptonuria, a genetic defect in human amino acid metabolism, specifically L-tyrosine and L-phenylalanine, was identified in 1859 and in 1891 the compound which accumulated and darkened urine was identified as homogentisic acid also known as dihydroxyphenylacetic acid (Textbook of Biochemistry with Clinical Correlations, Pp. 589 to 591, T. M. Devlin, Ed., Wiley, 1982, New York). Subsequent research has shown that dietary amino acid imbalance, that is tyrosine-rich or protein-rich foods, can also interfere with the normal human and mammalian metabolism of tyrosine and phenylalanine and thus result in the excretion of homogentisic acid (Neuberger et al. in Biochem. J. 44, 1945, Pp. 438–449; Neuberger, A. and Webster, T. A. in Biochem. J. 41, 1947, Pp 449–457). Microorganisms, among them certain fungi, are also able to assimilate tyrosine and phenylalanine, and in some cases as the sole source of carbon. Genetic defects can also perturb the amino acid pathways in these organisms and result in the accumulation of metabolic intermediates. Fungi which break down tyrosine or phenylalanine via homogentisic acid, an established pathway for amino acid catabolism, would be expected to accumulate homogentisic acid if the appropriate genetic mutation prevented its further degradation to other compounds. A mutant for the fungus *Yarrowia lipolytica* has been isolated which does in fact display this phenomenon and excretes homogentisic acid owing to a defect in tyrosine and phenylalanine metabolism. The use of a suboptimal D-glucose concentration of 0.5% when propagating this mutant strain permits rapid growth and generation of yeast biomass, but also limits the levels of this preferred carbon source at later stages of growth, thus promoting subsequent utilization and biotransformation of L-tyrosine and L-phenylalanine to homogentisic acid.

The present invention involves the biotransformation of biological substances to homogentisic acid (2,5-dihydroxyphenylacetic acid) which can, if desired, be polymerized in place to form a melanin pigment. It has been discovered that *Yarrowia lipolytica* mutant YB3-180 has the ability to convert either L-tyrosine or L-phenylalanine to homogentisic acid. This strain has been deposited with the American Type Culture Collection under the term of the Budapest Treaty and been assigned accession number 20875. The carbon source used to support cell growth can be either a carbohydrate, such as D-glucose, or a hydrocarbon, such as hexadecane. This biotransformation is at least 40% efficient (in terms of conversion of the amino acid(s) to homogentisic acid) in aerated, synthetic medium with 0.5% D-glucose and 5 mM L-tyrosine or L-phenylalanine and results in the secretion of homogentisic acid into the culture medium.

When the culture fluid produced by hexadecane or D-glucose nurtured cells is made alkaline, the homogentisic acid derived from the amino acid is rapidly and non-enzymatically converted into a melanin pigment. Homogentisic acid and the melanin pigment can also be produced in a rich medium containing D-glucose along with yeast extract and peptone as the source of amino acids since peptone consists of peptides and proteins which contain amino acids such as L-tyrosine and L-phenylalanine. Under these circumstances, pigment is formed without the need for pH adjustment. Furthermore, Bacillus spp. that excrete aromatic amino acids can also serve as the source of substrate for the biotransformation when these organisms are cultured with *Y. lipolytica*. Thus, microorganisms that excrete L-tyrosine or L-phenylalanine and can be cultured with *Y. lipolytica* can be used as a source for the amino acid substrates.

The present invention also involves the extraction and purification of homogentisic acid from *Y. lipolytica* culture medium by the addition of ethyl acetate thereto with subsequent crystallization. Ion exchange chromatography is also effective in isolation of both homogentisic acid and its reaction product, the melanin pigment.

The *Y. lipolytica* mutant ATCC (20875) used in the preparation of homogentisic acid as described in the following examples was derived from YB 3-122 (inositol-requiring), which was derived from ATCC 18943 (NRRL YB423-3) (also known as YB 423-3). YB 3-180 is a spontaneous mutant that appeared upon plating on nutrient medium with inositol of YB 3-122 and observation of a brown color to facilitate screening from its immediate parent strains ATCC 18943 (NRRL YB423-3) (wild type) and YB 3-122 (inositol-requiring). The mutant was derived as a spontaneous mutant of strain YB3-122 which was derived from ATCC 18943 by mutagenesis with ethylmethane sulfonate. The biotransformation described herein is possible because mutant ATCC (20875), unlike its parent strains, is unable to utilize L-tyrosine as the sole carbon source. Once the D-glucose has been assimilated and used to generate cell mass, L-tyrosine is catabolized. Homogentisic acid, a recognized intermediate in L-tyrosine and L-phenylalanine degradation, accumulates in the culture medium as a result of a biochemical block in the pathway for the breakdown of these amino acids.

Melanin pigment production in culture medium or with purified homogentisic acid is possible since the acid polymerizes spontaneously under alkaline conditions to yield this material which is characteristically brown in color. This color coupled with the favorable regulatory status of fungal strains of the species *Y. lipolytica* renders the melanin pigment suitable for use as an alternative to caramel color in beverage applications or in cosmetic applications.

Homogentisic acid can be prepared on a laboratory scale by growing *Y. lipolytica* ATCC (20875) in a shaker incubator at 28° C. in aerated, defined minimal salts medium (supplemented with inositol) containing 0.5% D-glucose and 5 mM L-tyrosine or 5 mM L-phenylalanine for 3 to 4 days. After removal of the biomass, such as by filtration or centrifugation, the acid can be concentrated in the cell free culture medium by rotary evaporation and extracted with ethyl acetate whereupon it is concentrated in vacuo to yield crystals. At least 40% of the available L-tyrosine is converted to homogentisic acid which product has been identified by mass spectroscopy and nuclear magnetic resonance.

EXAMPLE I

Preparation of Homogentisic Acid (HA) from L-tyrosine

A 1.25 l culture of *Yarrowia lipolytica* mutant strain ATCC 20875 was grown in a 2.8 l Fernbach flask incubated in a New Brunswick incubator-shaker at 28° C. and rotated at 225 rpm. The inoculum had been grown overnight in 25 ml of liquid nutrient medium of the following composition where nutrient rich medium is an undefined medium which contains extracts of other organisms such as yeast or beef and synthetic minimal medium is a chemically defined medium.

| Nutrient Rich Medium (Undefined) | | |
|---|---|---|
| for one liter of medium | 10 g yeast extract | 10 g |
| | 20 g peptone | 20 |
| | D-glucose | 20 |
| | deionized water | 1000 ml |
| Synthetic Minimal Medium (Defined) | | |
| for one liter of medium | SALTS | |
| | potassium phosphate (monobasic) | 1 g |
| | NaCl | 0.1 |
| | $CaCl_2$ | 0.1 |
| | VITAMINS | |
| | biotin | 2 μg |
| | calcium pantothenate | 400 |
| | folic acid | 2 |
| | niacin | 400 |
| | p-aminobenzoic acid | 200 |
| | pyridoxine-HCl | 400 |
| | riboflavin | 200 |
| | thiamin-HCl | 400 |
| | TRACE ELEMENTS | |
| | boric acid | 0.5 mg |
| | $CuSO_4$ | 0.04 |
| | KI | 0.1 |
| | $FeCl_3$ | 0.2 |
| | $MnSO_4$ | 0.4 |
| | $NaMoO_4$ | 0.2 |
| | $ZnSO_4$ | 0.4 |
| | OTHER ADDITIONS | |

| -continued | |
|---|---|
| $MgSO_4$ | 0.5 g |
| ammonium sulfate | 5 g |
| myo-inositol | 2 mg |
| D-glucose | 5 g |
| deionized water | 1000 ml |
| AROMATIC AMINO ACIDS, | |
| L-tyrosine or L-phenylalanine added if desired. | |

After propagation, the cells were centrifuged and washed twice with sterile water. A Fernbach flask containing a synthetic medium supplemented with 5 mM L-tyrosine was inoculated to provide a concentration of $1 \times 10^5$ cells per ml. After 5 days of incubation in the shaker-incubator, the cells were removed by centrifugation, the pH of the supernatant was adjusted to pH 3.0 with $H_2SO_4$ and the culture fluid was filter sterilized with a 0.45μ filter unit. The clear solution was stored at 0°–5° prior to analysis.

The culture fluid obtained as described above was concentrated by rotary evaporation, extracted with ethyl acetate and concentratd in vacuo to yield crystals of homogentisic acid. Quantitative analysis revealed that at least 40% of the L-tyrosine supplemented to the minimal salts medium was converted to homogentisic acid. The yield of homogentisic acid was found to be proportional to the amount of L-tyrosine supplied. Qualitative analysis of the final product by mass spectroscopy and nuclear magnetic resonance both indicated that the prpoduct was homogentisic acid.

The final preparation of culture fluid obtained with L-tyrosine grown cells can be rapidly converted to a solution of brown melanin pigment by adjustment of the pH to 10 with $NH_4OH$. The same observation is made when a culture fluid obtained from cells grown with L-phenylalanine is treated with a neutralizing agent. Wild type *Y. lipolytica* ATCC 18943 and mutant YB3-122 produce only trace amounts (less than 0.1% that of the mutant) of brown color under similar conditions because they are able to grow on L-tyrosine as the sole carbon source.

EXAMPLE II

Preparation of Melanin Pigment via Homogentistic Acid in Nutrient Medium

*Y. lipolytica* mutant strain ATCC 20875 was grown in the nutrient medium described above to produce homogentisic acid and melanin pigment. During yeast growth protein constituents (peptone) of the nutrient medium were degraded, thereby liberating L-tyrosine and L-phenylalanine. Catabolism of these and the other amino acids released ammonia thereby raising the pH of thd medium to 11 after about 5 days. Due to this pH change, the excreted homogentisic acid polymerized causing the culture medium to turn dark brown. The polymerization was dependent on aeration and alkaline conditions. Melanin pigment was precipitated with three volumes of acetone; at least 35 mg of brown pigment per liter of nutrient medium could be recovered after dialysis and lyophilization of the culture medium. Melanin pigment prepared in this manner shared properties with material obtained using the synthetic medium described in Example I.

What is claimed is:

1. A method for the production of a melanin pigment which is the polymerization product of homogentisic acid which method comprises growing a fungus which has been mutated to provide a strain which is unable to grow on L-tyrosine and/or L-phenylalanine as the sole carbon source in a nutrient growth medium or a synthetic minimal medium containing a polypeptide containing one or both of these amino acids which medium contains a sub-optimal concentration of carbohydrate assimilable by the fungus, for a period of time and under conditions suitable for the degradation of the polypeptide thereby liberating L-tyrosine, L-phenylalanine and other amino acids resulting in the production of homogentisic acid and to permit the catabolism of the liberated amino acids to form ammonia thereby raising the pH of the medium to a level of at least about 10 to cause the homogentisic acid to polymerize thereby forming the melanin pigment.

2. The method of claim 1 wherein the fungus is a yeast of the species *Yarrowia lipolytica*.

3. The method of claim 2 wherein the yeast is *Y. lipolytica* ATCC (ATCC 20875).

* * * * *